US009381222B2

(12) United States Patent
Jeong et al.

(10) Patent No.: US 9,381,222 B2
(45) Date of Patent: Jul. 5, 2016

(54) COMPOSITIONS FOR PREVENTING AND TREATING OBESITY, HYPERLIPIDEMIA, ATHEROSCLEROSIS, FATTY LIVER, DIABETES OR METABOLIC SYNDROME CONTAINING EXTRACTS OF GLYCINE MAX LEAVES OR FRACTIONS ISOLATED FROM THE SAME AS AN ACTIVE INGREDIENT

(75) Inventors: Tae-Sook Jeong, Daejeon (KR); Woo Song Lee, Jeollabuk-do (KR); Ki Hun Park, Gyeongsangnam-do (KR); Myung-Sook Choi, Daegu (KR); Ho Yong Park, Daejeon (KR); Jong-Min Han, Daejeon (KR); Hyung-Jae Jeong, Gyeongsangnam-do (KR)

(73) Assignee: Korea Reasearch Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/615,602

(22) Filed: Nov. 10, 2009

(65) Prior Publication Data

US 2010/0291248 A1 Nov. 18, 2010

(30) Foreign Application Priority Data

May 12, 2009 (KR) ........................ 10-2009-0041321

(51) Int. Cl.
*A61K 36/48* (2006.01)
(52) U.S. Cl.
CPC ..................... *A61K 36/48* (2013.01)
(58) Field of Classification Search
CPC ....................................................... A61K 36/48
USPC ................................................ 424/757, 774
See application file for complete search history.

(56) References Cited

FOREIGN PATENT DOCUMENTS

| KR | 10-2001-0071541 A1 | 7/2001 |
|---|---|---|
| KR | 439147 B1 | 8/2002 |
| KR | 500641 B1 | 1/2004 |
| KR | 10-2007-0070303 * | 7/2007 |

OTHER PUBLICATIONS

Ho (J. Agric. Food Chem (2003), vol. 51, pp. 4554-4558).*

Rudel, et al., "Acyl coenzyme A: cholesterol acyltransferase types 1 and 2: structure and function in atherosclerosis", Curr. Opin. Lipidol, 2001, pp. 121-127, vol. 12, Lippincott Williams & Wilkins.
Buhman, et al., "Resistance to diet-induced hypercholesterolemia and gallstone formation in ACAT2-deficient mice", Nature Medicine, Dec. 2000, pp. 1341-1347, vol. 6, No. 12, Nature America Inc.
Hakkinen, et al., "Lipoprotein-Associated Phospholipase A2, Platelet-Activating Factor Acetylhydrolase, Is Expressed by Macrophages in Human and Rabbit Atherosclerotic Lesions", Arterioscler. Thromb. Vasc. Biol., Dec. 1999, pp. 2909-2917, vol. 19, American Heart Association, Inc.
XIIth International Symposium on Atherosclerosis, Workshop Abstracts, Jun. 2000, p. 166, vol. 151, Stockholm, Sweden.
Packard, et al., "Lipoprotein-Associated Phospholipase $A_2$ as an Independent Predictor of Coronary Heart Disease", The New England Journal of Medicine, Oct. 19, 2000, pp. 1148-1155, vol. 343, No. 16.
Lee, et al., "Phytochemical Constituents from the Leaves of Soybean [Glycine max (L.) Merr.]", Food Science and Biotechnology, 2008, pp. 578-586, vol. 17, No. 3.
Ho, et al., "Difference in flavonoid and isoflavone profile between soybean and soy leaf", Biomedicine & Pharmacotherapy, Apr. 2002, pp. 289-295, vol. 56, Editions scientifiques et medicales Elsevier SAS.
Lee, et al., "Triterpenoids from Roots of Glycine max (L.) Merr.", Agric. Chem. Biotechnol. May 2006, pp. 51-56, vol. 49, No. 2.
Lee, et al., "LDL-Antioxidant Pterocarpans from Roots of Glycine max (L.) Merr.", Journal of Agricultural and Food Chemistry, 2006, pp. 2057-2063, vol. 54, American Chemical Society.
Lee, et al., "Human Acyl-CoA: Cholesterol Acyltransferase (hACAT) Inhibitory Activities of Triterpenoids from Roots of Glycine max (L.) Merr.", Bull. Kor. Chem. Soc., 2008, pp. 615-619, vol. 29, No. 3.
Klejdus, et al., "Evaluation of Isoflavone Aglycon and Glycoside Distribution in Soy Plants and Soybeans by Fast Column High-Performance Liquid Chromatography Coupled with a Diode-Array Detector", Journal of Agricultural and Food Chemistry, 2005, pp. 5848-5852, vol. 53, American Chemical Society.
Ho et al. (2002) "Vascular Effects of Soy Leaves (*Glycine max*) Extract and Kaempferol Glycosides in Isolated Rat Carotid Arteries," Planta Med 68:487-491.
Yu et al., "3-O-β-D-glucosyl-(1→6)-β-D-glucosyl-kaempferol Isolated from *Sauropus androgenus* Reduces Body Weight Gain in Wistar Rats", Biol. Pharm. Bull., 2006, vol. 29(12), pp. 2510-2513.

* cited by examiner

*Primary Examiner* — Susan Hoffman
(74) *Attorney, Agent, or Firm* — Lathrop & Gage LLP

(57) ABSTRACT

The present invention relates to compositions for preventing and treating obesity, hyperlipidemia, atherosclerosis, fatty liver, diabetes or metabolic syndrome containing extracts of *Glycine max* leaves or fractions isolated from the same.

11 Claims, 2 Drawing Sheets

COMPOSITIONS FOR PREVENTING AND TREATING OBESITY, HYPERLIPIDEMIA, ATHEROSCLEROSIS, FATTY LIVER, DIABETES OR METABOLIC SYNDROME CONTAINING EXTRACTS OF GLYCINE MAX LEAVES OR FRACTIONS ISOLATED FROM THE SAME AS AN ACTIVE INGREDIENT

CROSS-REFERENCES TO RELATED APPLICATION

This patent application claims the benefit of priority under 35 U.S.C. §119 of Korean Patent Application No. 10-2009-0041321 filed on May 12, 2009, the contents of which are incorporated herein by reference.

BACKGROUND OF THE INVENTION

1. Field of the Invention

The present invention relates to compositions for preventing and treating of obesity, hyperlipidemia, atherosclerosis, fatty liver, diabetes or metabolic syndrome containing extracts of G. max leaves or fractions isolated from the same.

2. Description of the Related Art

Obesity, one of chronic diseases suffered by modern people, is rising as a serious health-threatening problem in the wave of industrialization and change of diet habit and life style resulted from the increase of income. In 1996, obesity was acclaimed as disease by WHO. Obesity is also known to be related directly or indirectly to adult diseases such as diabetes, hypertension, hyperlipidemia, and heart disease and various types of cancer.

The mechanisms of anti-obesity agents known so far are appetite suppression, thermogenesis acceleration, diuretic action, digestion inhibition, and hormone regulation. Reductil (Reductil™, Abbott, USA), one of the most widely used anti-obesity agents, is an appetite suppressant, which forms over a hundred million dollar market in USA. However, such appetite suppressant therapy for treating obesity has side effects such as hypertension, diarrhea, constipation, insomnia and anxiety. Therefore, it is urgently required to develop a drug for the prevention and treatment of obesity that has less side effects but has excellent stability for long term administration.

With the increase of adult diseases, cardiovascular diseases are recently rising significantly. One of the most representative cardiovascular diseases is atherosclerosis, which is the inflammatory disease progressed by the lipid accumulation and fibrous-cap formation in artery wall. Hypertension, smoking, obesity and the increase of low-density lipoprotein (LDL) seem to be major reasons for atherosclerosis. Atherosclerosis is easily developed in cerebral artery or coronary artery, which progresses to circulatory disease such as heart disease and cerebrovascular disease.

Acyl-CoA:cholesterol acyltransferase (ACAT) plays an important role in esterification of cholesterol. Particularly, ACAT converts cholesterol to its ester form to accumulate cholesterol in cells. The human ACAT exists as two isoenzymes, ACAT-1 and ACAT-2. Human ACAT-1 (50 kDa) works in adult liver, adrenal gland, macrophage and kidney, while human ACAT-2 (46 kDa) works in small intestines (Curr. Opin. Lipidol. 12: 121-127, 2001). ACAT inhibitors can inhibit the absorption of cholesterol taken from food and inhibit the accumulation of cholesteryl ester in vascular endothelial cells, so that it can be a target material for the prevention and treatment of hypercholesterolemia, cholesterol gallstones or atherosclerosis (Nature Med. 6, 1341-1347, 2000).

Lipoprotein-associated phospholipase $A_2$ (Lp-PLA$_2$) is an independent risk factor causing coronary artery disease in hypercholesterolemia patients, and is proposed as a pro-inflammatory agent. Lp-PLA$_2$ has been identified in macrophages of atherosclerotic lesions (Arterioscler. Thromb. Vasc. Biol. 19: 2909-2971, 1999). According to recent studies, the administration of Lp-PLA$_2$ inhibitor decreases significantly the fatty streak formation of Watanabe heritable hyperlipidemic rabbit, an atherosclerotic animal model (Atherosclerosis, 151: 166, 2000). Thus, Lp-PLA$_2$ inhibitor has become a target for the prevention and treatment of atherosclerosis (N. Engl. J. Med. 343: 1148-1155, 2000). It is believed that the development of Lp-PLA$_2$ inhibitor is a very important task for the prevention and treatment of atherosclerosis.

Metabolic syndrome is also known as insulin resistance syndrome, which is closely related to obesity, type II diabetes, hypertension, hypertriglyceridemia, hypercholesterolemia, and atherosclerosis. In particular, the reason why metabolic syndrome has been a major concern in our society is that it might cause various vascular diseases caused by atherosclerosis that destroy the quality of life in a patient or make matter worse to cause early death of a patient. Therefore, it is very important to diagnose early and to treat the increasing metabolic syndrome and further to prevent the same.

Soybean (*Glycine max* (L.) Merr.) is annual plant belonging to the Leguminosae (Fabaceae) family and widely distributed in Asia, Africa, and Australia. This plant has been widely cultivated as edible plant. Soybean is rich in protein and lipid and also contains many bioactive materials, so that it can inhibit the development of coronary heart disease, breast cancer, prostatic cancer, and colon cancer. Studies for the prevention of adult disease using soybean have been undergoing. Soybean root is also a medicinal material used in Korean traditional medicine and folk remedy. The conventional arts in relation to using soybean root are described in Korean Patent No. 500641 relating to food for promoting hair growth, Korean Patent No. 439147 relating to the compositions for care of skin suffering from acne or seborrhea, and Korean Patent Publication No. 2001-0071541 relating to the composition for the prevention and/or treatment of osteoporosis and alterations due to menopause syndrome.

Much research has been devoted to the composition of soybean leaves (*G. max* leaves). As shown in Table 1 and FIG. 1, the composition of soybean leaves (*G. max* leaves) is different from that of soybean, soybean stems or roots (Food Sci. Biotechnol. 17: 578-586, 2008; Biomed. Pharmacother. 56: 289-295, 2002; Agric. Chem. Biotechnol. 49: 51-55, 2006; J. Agric. Food Chem. 54. 2057-2063, 2006; Bull. Kor. Chem. Soc. 29: 615-619, 2008).

TABLE 1

| Compounds | Soybean leaves | Soybean | Soybean roots |
|---|---|---|---|
| daidzein (4',7-dihydroxyisoflavone) | ○ | ○ | ○ |
| genistein (4',5,7-trihydroxyisoflavone) | ○ | ○ | ○ |
| genistin (4',5,7-Trihydroxyisoflavone-7-O-β-D-glucopyranoside) | ○ | ○ | ND |
| glycitein (4',7-Dihydroxy-6-methoxyisoflavone) | ○ | ○ | ○ |

TABLE 1-continued

| Compounds | Soybean leaves | Soybean | Soybean roots |
|---|---|---|---|
| 6'-O-malonyldaidzin | o | o | ND |
| 6'-O-malonylgenistin | o | o | ND |
| kaempferol-3-O-α-L-rhamnopyranosyl(1→2)-β-D-glucopyranosyl(1→6)-β-D-galactopyranoside | o | ND | ND |
| kaempferol-3-O-(2,6-di-O-α-rhamnopyranosyl)-β-galactopyranoside | o | ND | ND |
| kaempferol-3-O-digalactopyranoside | o | ND | ND |
| Kaempferol-3-O-diglucopyranoside | o | ND | ND |
| kaempferol-3-O-α-L-rhamnopyranosyl(1→6)-β-D-galactopyranoside | o | ND | ND |
| kaempferol-3-O-rutinoside | o | ND | ND |
| 3',4',5,7-tetrahydroxyflavone | o | ND | ND |
| 3',4',5-trihydroxyflavone-7-O-β-D-glucopyranoside | o | ND | ND |
| 3',4',5,7-tetrahydroxyflavonol | o | ND | ND |
| coumestrol | o | o | ND |
| glyceofuran | o | o | ND |
| 4-hydroxybenzoic acid | o | ND | ND |
| methyl-4-hydroxybenzoate | o | ND | ND |
| soysapogenol B | o | ND | ND |
| stigmasterol | o | o | ND |
| D-mannitol | o | ND | ND |
| 5,7,4'-trihydroxyflavone | o | ND | ND |
| isoformononetin (4'-Hydroxy-7-methoxyisoflavone) | o | ND | ND |
| 3-O-[α-L-rhamnopyranosyl-(1→2)-[β-D-glucopyranosyl-(1→6)]-β-D-glucopyranoside] | o | ND | ND |
| fluorocitric acid | o | ND | ND |

* ND: not detected

The contents of major components of *G. max*, isoflavone aglycons and glycosides (Daidzein, Glycitein, Genistein, Genistin, Daidzin, and Glycitin) are significantly decreased in soybean>soybean roots>soybean leaves (*G. max* leaves) (harvested after at least 90 days of cultivation) in that order (J. Agric. Food Chem. 53: 5848-5852, 2005). Therefore, the composition containing extracts of *G. max* leaves or fractions isolated from the same as an active ingredient contains other components than isoflavone aglycons and glycosides found in soybean or soybean roots. *G. max* leaves contain lots of kaempferol glycosides, but the effects of *G. max* leaves containing kaempferol glycosides has not been reported.

While searching a new anti-obesity agent from natural resources having less side effects, the present inventors figured out that the extracts of *G. max* leaves or fractions isolated from the same reduce body fat, blood cholesterol, triglyceride, glucose, insulin and hepatoxicity index enzyme level, inhibit the accumulation of fat in liver tissues, and inhibit the formation of artery lesion in cardio artery, so that they can be effectively used for the prevention and treatment of obesity, hyperlipidemia, atherosclerosis, fatty liver, diabetes or metabolic syndrome, leading to the completion of this invention.

SUMMARY OF THE INVENTION

It is an object of the present invention to provide a pharmaceutical composition for preventing and treating obesity, hyperlipidemia, atherosclerosis, fatty liver, diabetes or metabolic syndrome containing the extracts of *G. max* leaves or fractions isolated from the same as an active ingredient.

To achieve the above object, the present invention provides a pharmaceutical composition for preventing and treating obesity, hyperlipidemia, atherosclerosis, fatty liver, diabetes or metabolic syndrome containing the extracts of *G. max* leaves extracted by using water, organic solvent or a mixed solvent thereof or fractions isolated from the same by using organic solvent as an active ingredient.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

The present invention provides a pharmaceutical composition for preventing or treating obesity, hyperlipidemia, atherosclerosis, fatty liver, diabetes or metabolic syndrome containing the extracts of *G. max* leaves or fractions isolated from the same as an active ingredient.

The extracts of *G. max* leaves of the present invention are preferably prepared by the method containing the following steps, but not limited thereto:

1) extracting *G. max* leaves using water, an organic solvent or a mixed solvent thereof; and
2) obtaining dried powder by concentrating the extract obtained in step 1) under a reduced pressure.

The *G. max* leaves in step 1) according to the above method may be the one cultured or purchased.

The organic solvent of step 1) according to the above method may be alcohol, ethyl acetate or acetonitrile. The alcohol is preferably $C_1$-$C_4$ lower alcohol and more preferably methanol, ethanol, propanol or isopropanol. Organic substances are easily eluted in 100% alcohol, while glycosides are easily eluted in aqueous solution with alcohol. So, alcohol or aqueous solution with alcohol can be properly selected. The solvent is added to *G. max* leaves 5-15 times the volume of the leaves for the extraction and more preferably added 10 times the volume of the leaves. Extraction is preferably performed at room temperature, but not limited thereto. The extraction is preferably repeated 1-5 times and more preferably repeated 3 times, but not limited thereto.

The processes of concentration under reduced pressure in step 2) are performed by the conventional method used by those in the art.

The fractions from the extracts of *G. max* leaves of the present invention are preferably prepared by the method containing the following steps, but not limited thereto:

1) concentrating the ethanol extracts of *G. max* leaves under a reduced pressure to obtain the resulting aqueous suspension;
2) obtaining fractions by partitioning the concentrated aqueous suspension of step 1) with an organic solvent; and
3) obtaining dried powder by concentrating the fraction obtained in step 2) under a reduced pressure.

The ethanol extracts of *G. max* leaves of step 1) is prepared by the said extraction method, but not limited thereto.

The organic solvents of step 2) are hexane and ethyl acetate, and added successively, but not limited thereto.

The fractions of step 2) are preferably obtained by fractionation using separatory funnel, but not limited thereto.

Figure 1:
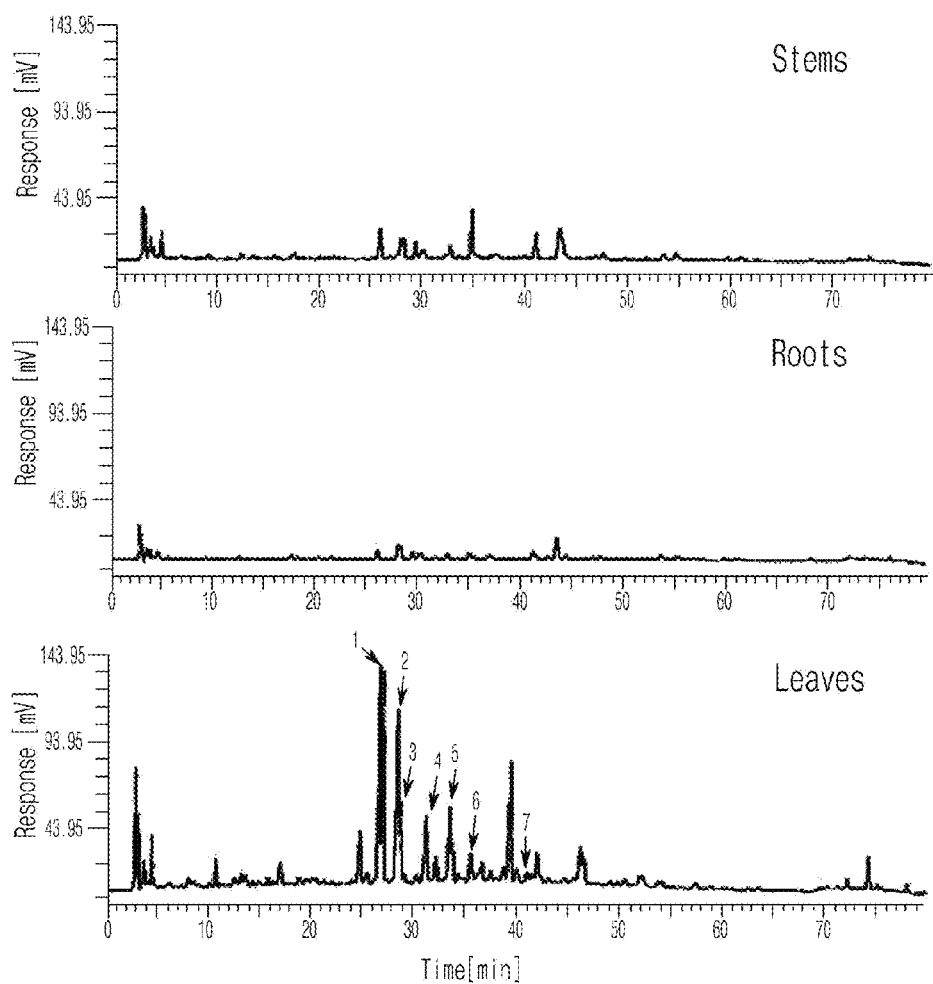
FIG. 1 is a set of graphs illustrating the results of HPLC analysis with the ethanol extracts of Soybean leaves (*G. max* leaves), Soybean roots and Soybean stems in a preferred embodiment of the present invention.

HPLC analysis confirmed that the extracts of *G. max* leaves or fractions isolated from the same of the present invention contained a large amount of kaempferol glycosides (see Table 2 and FIG. 1).

The effects of the extracts of *G. max* leaves or fractions isolated from the same according to the present invention on the activities of ACAT and Lp-PLA$_2$ were investigated. As a result, these extracts or fractions demonstrated equal or 20~60% higher inhibitory effect on ACAT and Lp-PLA$_2$ than the extracts of soybean or Soybean roots (see Table 3 and Table 4). Therefore, the extracts of *G. max* leaves or fractions isolated from the same according to the present invention can be effectively used for the prevention and treatment of atherosclerosis by effectively inhibiting ACAT and Lp-PLA$_2$.

Experimental animals were randomly divided and grouped into the negative control group (ND) fed by normal diet, the control group (HFHC) fed by high-fat high-cholesterol diet and the experimental group fed by high-fat high-cholesterol diet with the extracts of *G. max* leaves or fractions isolated from the same according to the invention. White adipose tissues (WAT) weight, total lipid amount in liver, plasma concentration of total cholesterol, HDL-cholesterol, triglyceride, phospholipid, glucose, and insulin, GOT, and GPT of each animal were measured after 12 weeks. As a result, the extracts of *G. max* leaves or fractions isolated from the same according to the present invention inhibited the increase of WAT (see FIG. 2 and Table 5), reduced the accumulation of total lipid in liver (see Table 6), and reduced plasma cholesterol, triglyceride, glucose, insulin and hepatotoxic index (GOT and GPT) (see Tables 7-9). Therefore, the extracts of *G. max* leaves or fractions isolated from the same according to the present invention can be effectively used for the prevention and treatment of obesity, fatty liver or diabetes.

The area of atherosclerotic lesions in aortic sinus was also measured. Compared with in the control group fed by high-fat high-cholesterol diet, the mean lesional area was significantly reduced in the experimental group treated with the extracts of *G. max* leaves or fractions isolated from the same according to the present invention (see Table 10). The above result indicates that the extracts of *G. max* leaves or fractions isolated from the same according to the present invention can be effectively used for the prevention or treatment of atherosclerosis owing to their excellent anti-atherosclerotic activities.

The above results suggest that the extracts of *G. max* leaves or fractions isolated from the same according to the present invention can be effectively used for the prevention or treatment of obesity, hyperlipidemia, atherosclerosis, fatty liver, diabetes or metabolic syndrome by inhibiting the adipose tissues growth resulted from high-fat diet, inhibiting the increase of cholesterol and triglyceride in plasma and liver, and reducing the formation of atherosclerotic lesions in aorta.

The composition of the present invention can be administered alone or treated together with surgical operation, hormone therapy, chemo-therapy and biological regulators for the prevention and treatment of obesity, hyperlipidemia, atherosclerosis, fatty liver, diabetes or metabolic syndrome.

The composition of the present invention can include one or more pharmaceutically acceptable carriers in addition to the active ingredient, such as saline, sterilized water, Ringer's solution, buffered saline, dextrose solution, maltodextrin solution, glycerol, ethanol, liposome and a mixture containing one or more of those components. The pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added. The composition of the present invention can be formulated in different drug forms including aqueous solutions, suspensions and emulsions for injection, pills, capsules, granules or tablets by mixing with diluents, dispersing agents, surfactants, binders and lubricants. The composition can further be prepared in suitable forms according to each disease or ingredient by following the method represented in Remington's Pharmaceutical Sciences (18$^{th}$ edition, Ed. Gennard, Alfonso R., Mack Publishing Company, Easton Pa., 1990).

The composition of the present invention can be administered orally or parenterally (for example, intravenous, hypodermic, peritoneal or local injection). The effective dosage of the composition can be determined according to body weight, age, gender, and health condition of a patient, diet, administration frequency, administration method, excretion rate and severity of a disease. The dosage of the extracts or fractions from the same according to the present invention is 500±200 mg/kg per day and preferably 400±100 mg/kg per day, and administration frequency is preferably 1-3 times a day.

ADVANTAGEOUS EFFECTIVENESS

The extracts of *G. max* leaves or fractions isolated from the same according to the present invention contain a large amount of kaempferol glycosides and can be effectively used for the prevention and treatment of obesity, hyperlipidemia, atherosclerosis, fatty liver, diabetes or metabolic syndrome by inhibiting the activities of cholesterol acyltransferase (ACAT) and Lp-PLA$_2$, by inhibiting the increase of high-fat diet-induced body fat, by inhibiting the increase of cholesterol and triglyceride in plasma and liver, and reducing the formation of atherosclerotic lesions in the aorta.

Practical and presently preferred embodiments of the present invention are illustrated as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of Extracts of *G. max* Leaves

<1-1> Ethanol Extracts of *G. max* Leaves

Soybeans were seeded in Jinju-si, Gyeongsangnam-do, Korea. After 90 days of growing, Soybean leaves (*G. max* leaves) were harvested and dried in the shade. The dried leaves were ground. 1 kg of the ground *G. max* leaves was extracted two times with 50 L of 95% ethanol for two days at room temperature. The extracts were filtered to recover ethanol-soluble part and combined. The combined ethanol extracts were concentrated under a reduced pressure, and the resulting ethanol extracts (181 g) of *G. max* leaves were obtained.

<1-2> Hot Water Extracts of *G. max* Leaves 100 g of the ground *G. max* leaves were extracted with 1 L of water for 2 hours at 85-90° C. The extraction was repeated twice. The obtained extracts were filtered by filter paper to eliminate precipitates, and then filtrates were obtained. The filtrates were concentrated under a reduced pressure, and the resulting hot water extracts (15 g) of *G. max* leaves were obtained.

<1-3> Methanol, Ethyl Acetate, Acetonitrile and Isopropanol Extracts of *G. max* Leaves Extractions were performed by the same manner as described above except that 80% methanol, 100% ethyl acetate, 100% acetonitrile and 100% isopropanol were used instead of 95% ethanol of Example <1-1>. As a result, 150 g of methanol extracts, 43 g of ethyl acetate extracts, 30 g of acetonitrile extracts and 116 g of isopropanol extracts were obtained.

Example 2

Preparation from Fractions of Extracts of *G. max* Leaves

The ethanol extracts of *G. max* leaves (181 g) obtained in Example <1-1> were suspended in 500 ml of water. Equal amount of hexane was added the aqueous suspension, followed by fractionation of water layer and hexane layer. The above procedure was repeated once again with water layer to fractionate hexane layer. After separating hexane layer, an equal amount of ethyl acetate was added to water layer, followed by fractionation. The above ethyl acetate fractionation was repeated once again. The fractions were concentrated under a reduced pressure, and the resulting hexane fraction (18 g) and ethyl acetate fraction (32 g), respectively, were obtained.

Comparative Example 1

Preparation of Ethanol Extracts of Soybean

Ethanol extracts of soybean were prepared by the same manner as described in Example <1-1> except that 1 kg of soybean (*G. max*) was used instead of *G. max* leaves.

Comparative Example 2

Preparation of Extracts of Soybean Roots and Fractions from the Same

Ethanol extracts of soybean roots were prepared by the same manner as described in Example <1-1> except that 1 kg of soybean roots was used instead of *G. max* leaves.

Then, ethyl acetate fraction of soybean roots was prepared by the same manner as described in Example 2 using the ethanol extracts of soybean roots obtained above.

Experimental Example 1

HPLC Analysis with Extracts of *G. max* Leaves

Following experiment was performed to compare/investigate ingredients of the extract of *G. max* leaves.

1 g of each soybean leaves (*G. max* leaves), roots and stems dried in the shade was put in a 50 ml-conical tube, and extracted with 20 ml of 80% methanol for 6 hours at room temperature. The extracts were filtered with filter paper (No. 6) and then filtered once again with 0.45 μm membrane filter. The extracts were separated and analyzed by HPLC (column: Spheri-5 RP-18, 5 mm, 250×4.6 mm; eluent: acetonitrile/water [40:60 (v/v)]; sample volume: 10 μl; elution speed: 1.0 ml/min; detection: UV 254 nm; HPLC machine: PE Series 200) and LC-Mass. The results were analyzed and compared with the previously reported data (Biomed. Pharmacother. 56: 289-295, 2002) and then presented in Table 2 and FIG. 1.

Table 2

| Compounds | Structures |
| --- | --- |
| kaempferol-3-O-α-L-rhamnopyranosyl(1→2)-β-D-glucopyranosyl(1→6)-β-D-galactopyranoside (1) | 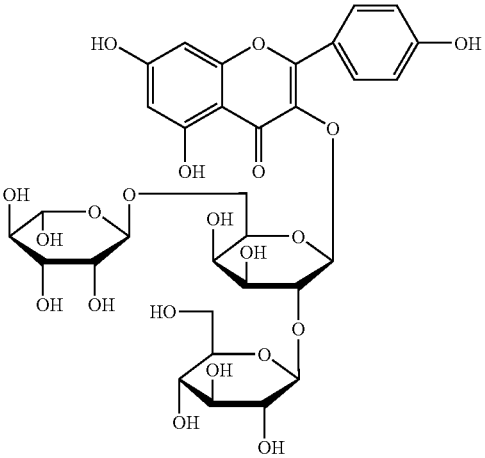 |

TABLE 2-continued

| Compounds | Structures |
|---|---|
| kaempferol-3-O-(2,6-di-O-α-rhamnopyranosyl)-β-galactopyranoside (2) | 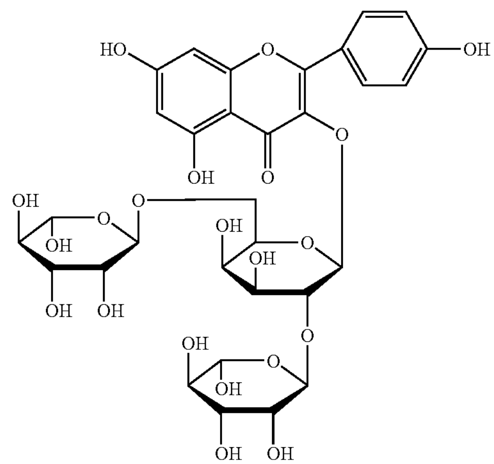 |
| kaempferol-3-O-digalactopyranoside (3) | 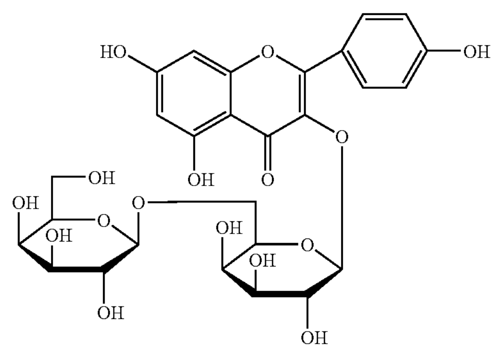 |
| kaempferol-3-O-α-L-rhamnopyranosyl(1→6)-β-D-galactopyranoside (4) | 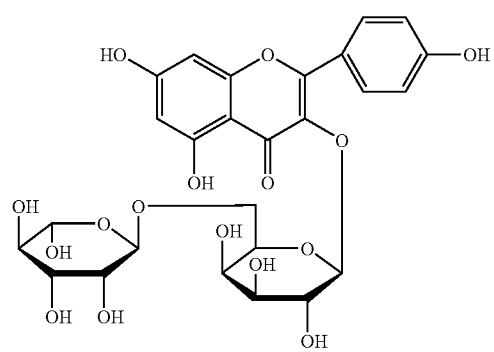 |
| kaempferol-3-O-rutinoside (5) | 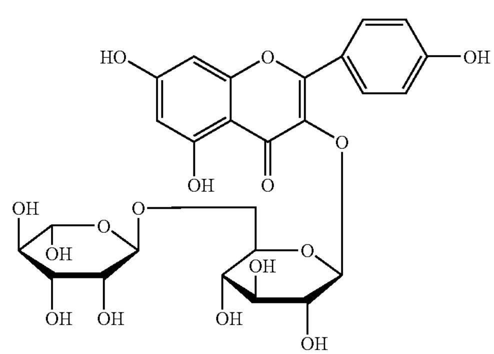 |

Table 2-continued

| Compounds | Structures |
|---|---|
| genistin (6) | 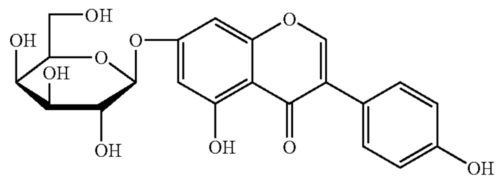 |
| 6'-O-malonylgenistin (7) | 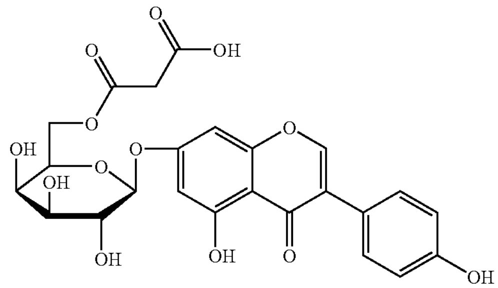 |

As shown in Table 2 and FIG. 1, the extracts of *G. max* leaves contained kaempferol glycosides more than the extracts of soybean roots and stems had. However, the contents of isoflavone and its glycosides (daidzein, glycitein, genistein, genistin, 6'-β-malonylgenistin, daidzin, and glycitin), which are the major ingredients of soybean (*G. max*), were very small.

Experimental Example 2

Measurement of ACAT Activity

Following experiment was performed to investigate the effect of the extracts of *G. max* leaves or fractions isolated from the same of the present invention on the activities of human ACAT-1 and ACAT-2.

cDNA of each of hACAT-1 and hACAT-2, obtained by human liver cDNA library screening, was inserted in baculovirus transfer vector, which was then introduced in sf9, the insect cell. Next, recombinant virus of each of hACAT-1 and hACAT-2 was separated by plaque purification. Viral stock titer was raised through three-time amplifications. Hi5, the insect cell showing higher protein expression rate, was infected with the recombinant virus to make multiplicity of infection (MOI)=1, followed by shaking-culture for one day at 27° C. The cultured Hi5 cells over-expressing hACAT-1 and hACAT-2 were collected by brief centrifugation at 500×g for 15 minutes. The cells were lysed by freezing-thawing in hypotonic buffer, followed by ultracentrifugation at 100,000×g for 1 hour at 4° C. to separate the microsomal fractions. The obtained microsomal fractions were suspended in hypotonic buffer to make protein concentration be 8 mg/ml, which were stored at −70° C. until use.

To measure hACAT-1 and hACAT-2 activities, the method of Brecher & Chan (P. Brecher and C. Chan, Biochem. Biophys. Acta, 617: 458, 1980) was used with a slight modification using [1-$^{14}$C] oleoyl-CoA as a substrate. The reaction mixture, containing 10 μl of each extracts and fractions of *G. max* leaves, root, and soybean obtained in the above example, 4.0 μl of the microsomal solution obtained above, 20.0 μl of assay buffer (0.5 M KH$_2$PO$_4$, 10 mM DTT, pH 7.4; Sigma), 15.0 μl of fatty acid-free BSA (bovine serum albumin, stock concentration 40 mg/Ml; Sigma), 2.0 μl of cholesterol (stock concentration 20 mg/Ml; Sigma), and 41.0 μl of distilled water, was preincubated for 15 minutes at 37° C. The reaction was initiated by the addition of 8 μl of [1-$^{14}$C] oleoyl-CoA (0.05 μCi, final conc. 10 μM, Amersham Biosciences). After 30 minutes of incubation at 37° C., the reaction was stopped by the addition of 1 μl of isopropanol-heptane (4:1, v/v solution. A mixture of 600 μl of heptane and 400 μl of 0.1 M potassium-phosphate saline (PBS, pH 7.4, 2 mM dithiothreitol) were added thereto. The above solution was mixed vigorously and centrifugated at 300×g for 5 minutes. Cholesteryl oleate was recovered in the upper heptane phase (total volume 0.9-1.0 Ml). The 100 μl of upper phase was put in a scintillation vial, to which 3 Ml of scintillation cocktail (Lumagel, Lumac Co.) was added. The radioactivity of cholesteryl [1-$^{14}$C] oleate generated from [[1-$^{14}$C] oleoyl-CoA was measured using liquid scintillation counter (1450 Microbeta Trilux, Wallacoy, Finland). Background values were obtained by preparing heat inactivated microsomes. The calculated hACAT-1 and hACAT-2 inhibitory activities are shown in Table 3.

TABLE 3

| | Inhibition at 100 μg/Ml (%) | |
|---|---|---|
| Samples | hACAT-1 | hACAT-2 |
| Ethanol extracts of soybean (*G. max*) | 33 | 31 |
| Ethanol extracts of *G. max* roots | 50 | 42 |
| Ethyl acetate fractions of ethanol extract of *G. max* roots | 62 | 55 |
| Ethanol extract of *G. max* leaves | 84 | 91 |
| Ethyl acetate extracts of *G. max* leaves | 95 | 98 |
| Acetonitrile extracts of *G. max* leaves | 94 | 93 |
| Isopropanol extracts of *G. max* leaves | 84 | 80 |
| Hexane fractions of ethanol extracts of *G. max* leaves | 97 | 97 |
| Ethyl acetate fractions of ethanol extracts of *G. max* leaves | 93 | 92 |

As shown in Table 3, the extracts and fractions of *G. max* leaves inhibited 80~98% hACAT-1 and hACAT-2 activities at the concentration of 100 μg/Ml, suggesting that they had 20~60% higher inhibitory effect than the extracts of soybean (*G. max*) (31~33%) or the extracts of soybean roots (42~62%).

The extracts and fractions of *G. max* leaves of the present invention have excellent inhibitory effect on human ACAT-1 and ACAT-2, so that they can be effectively used for the prevention or treatment of cardiovascular diseases including hyperlipidemia, coronary artery disease, atherosclerosis, and myocardial infarction induced from the synthesis and accumulation of cholesteryl ester.

Experimental Example 3

Measurement of Lp-PLA$_2$ Activity

Following experiment was performed to investigate the effect of the extracts of *G. max* leaves or fractions isolated from the same of the present invention on Lp-PLA$_2$ activity.

Lp-PLA$_2$ inhibitory effect was measured by the method of Boyd, et al. (Bioorg. Med. Chem. Lett. 10: 2557-2561, 2000) with a slight modification. LDL isolated from human plasma was used as Lp-PLA$_2$ enzyme sources. Lp-PLA$_2$ activity was measured using [$^3$H] platelet-activating factor (PAF) as a substrate. Briefly, a micelle substrate was prepared with unlabeled PAF and [$^3$H] PAF (100 µCi/Ml, 21.5 Ci/mmol, NET 910) in 10 mM PBS (pH 7.4), containing 2.7 mM EDTA (PBS-EDTA). The reaction mixture, containing 20 µl of diluted human LDL (4-5 lg protein), 120 µl of PBS-EDTA, and 20 µl of test sample, was preincubated for 15 min at 37° C. The reaction was initiated by the addition of 40 µl micelle substrate (0.05 µCi, final conc. 80 µM PAF). The reaction was stopped by vortexing with 600 µl of CHCl$_3$/MeOH (2:1, v/v) and the CHCl$_3$ and aqueous layers were separated by centrifugation. The upper aqueous layer (250 µl) was removed and mixed with 250 µl of CHCl$_3$. The 100 µl of final supernatant was put in a scintillation vial, to which 3 Ml of scintillation cocktail (Lumagel, Lumac Co.) were added. The radioactivity of [$^3$H] acetate generated from [$^3$H]PAF (1-O-hexadecyl-acetyl-3H(N)-phosphatidylcholine) was measured using liquid scintillation counter (1450 Microbeta Trilux, Wallacoy, Finland). The raw counts were corrected for background using a nonenzyme-containing blank. The results are shown in Table 4.

TABLE 4

| | Inhibition of Lp-PLA$_2$ at 200 µg/Ml (%) |
|---|---|
| Ethanol extracts of soybean (*G. max*) | 9 |
| Ethanol extracts of *G. max* roots | 28 |
| Ethanol extracts of *G. max* leaves | 48 |
| Ethyl acetate extracts of *G. max* leaves | 65 |
| Acetonitrile extracts of *G. max* leaves | 16 |
| Isopropanol extracts of *G. max* leaves | 44 |
| Hexane fractions of ethanol extracts of *G. max* leaves | 27 |
| Ethyl acetate fractions of ethanol extracts of *G. max* leaves | 45 |

As shown in Table 4, the extracts and fractions of *G. max* leaves inhibited 16~65% Lp-PLA$_2$ activity at the concentration of 200 µg/ml, suggesting that they had equal or higher inhibitory effects than the extracts of soybean (*G. max*) (9%) or the extracts of soybean roots (28~48%). In particular, the ethyl acetate extracts of *G. max* leaves showed excellent Lp-PLA$_2$ inhibitory activity (65%).

Therefore, the extracts and fractions of *G. max* leaves inhibit effectively the generation of lysophosphatidylcholine and free-oxidized fatty acid, the products of Lp-PLA$_2$ activation and inflammatory mediators. The extracts and fractions of *G. max* leaves of the present invention can be effectively used for the prevention or treatment of inflammatory diseases and cardiovascular diseases including hyperlipidemia, coronary artery disease, atherosclerosis, and myocardial infarction.

Experimental Example 4

Anti-Obese Effects

Following experiment was performed to investigate the effect of the extracts of *G. max* leaves or fractions isolated from the same of the present invention on obesity.

<4-1> Experimental Animals

Homozygous male LDL receptor deficient (LDLR$^{-/-}$, C57BL/6J background) mice were purchased from Jackson Laboratory (Bar Harbor, Me.) and housed in a room having controlled temperature (25±2° C.), humidity (50%±5%) and lighting (alternating 12 h periods of light and dark) at the Korea Research Institute of Bioscience and Biotechnology (KRIBB). The animals were adapted to the new environment with providing a normal diet (AIN-76A diet) and water freely for 2 weeks. Ten week-old male LDLR$^{-/-}$ mice were divided as follows.

(1) negative control group (ND) fed with a normal diet (AIN-76A diet);

(2) control group (HFHC or Control) fed with high-fat high-cholesterol diet (HFHC diet, a Western diet of 21% milk fat and 0.15% cholesterol by weight with no cholic acid: Dyets Inc., PA);

(3) experimental group 1 (EGML) fed with a HFHC diet supplemented with the ethanol extracts of *G. max* leaves of the present invention (1%, wt/wt diet);

(4) experimental group 2 fed with a HFHC diet supplemented with the water extracts of *G. max* leaves of the present invention (1%, wt/wt diet);

(5) experimental group 3 fed with a HFHC diet supplemented with the hexane fractions of *G. max* leaves extracts of the present invention (0.5%, wt/wt diet); and (6) experimental group 4 fed with a HFHC diet supplemented with the ethyl acetate fractions of *G. max* leaves extracts of the present invention (0.5%, wt/wt diet).

Lipid-lowering, anti-atherosclerotic and anti-obese effects were observed in the experimental groups for 12 weeks.

The mice were grouped 3~4 mice per a cage and housed in a room having controlled temperature (25±2° C.), humidity (50%±5%) and lighting (alternating 12 h periods of light and dark) at the Korea Research Institute of Bioscience and Biotechnology (KRIBB). The mice were given water and food ad libitum. Mice were treated in accordance with the KRIBB Guide for the Care and Use of Laboratory Animals.

Food intake and body weight were monitored at regular intervals. Blood was collected from the inferior vena cava into an EDTA-coated tube using capillary tube during feeding periods every week. There was a 12 h fast prior to euthanasia. Blood samples centrifuged at 8,000×g for 5 minutes at 4° C. within 30 minutes from the sampling. Collected plasma were stored at −70° C. until use. Following blood collection, all mice were anesthetized with thiopental sodium (Choong-wae Pharma Co., Seoul, Korea) and organ tissues (liver, small intestine, brain, aorta and adipose tissues) of each mouse were taken and then weighed. The tissues were frozen in liquid N$_2$ and stored at −70° C. until use.

<4-2> Measurement of Adipose Tissue Weight

Abdominal, epididymal and inguinal adipose tissues were extracted from each mouse of Experimental Example <4-1>. The weights of those adipose tissues were measured and the weight of adipose tissue/kg body weight was calculated. The weights of those adipose tissues are presented as mean±standard deviation (SD). Statistical analysis was done using Student's t-test. Values of p<0.05 were considered significant. The results are shown in Table 5 and FIG. 2.

TABLE 5

| Experimental groups | Relative weights of total fat (g/kg body weight) |
|---|---|
| Normal diet group (ND) | 168.2 ± 0.4 |
| Control group (HFHC) | 206.7 ± 6.0[#] |
| Experimental group 1 (HFHC + ethanol extracts of G. max leaves, EGML) | 137.0 ± 5.6[#,*] |
| Experimental group 2 (HFHC + water extracts of G. max leaves) | 170.2 ± 0.5* |
| Experimental group 3 (HFHC + hexane fractions of G. max leaves) | 148.8 ± 4.7* |
| Experimental group 4 (HFHC + ethyl acetate fractions of G. max leaves) | 135.1 ± 4.3[#,*] |

[#] $P < 0.05$ compared with ND
* $P < 0.05$ compared with HFHC

Figure 2:
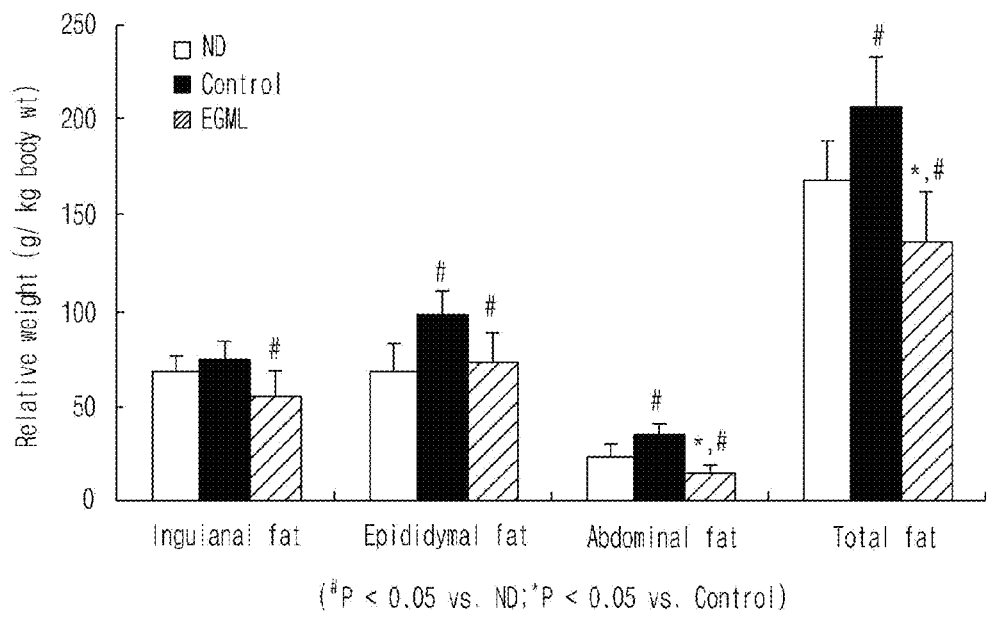
FIG. 2 is a graph illustrating the changes of white adipose tissue weight of an obese mouse model induced by High-fat high-cholesterol (HFHC) diet according to the administration of the ethanol extract of *G. max* leaves in a preferred embodiment of the present invention.

As shown in FIG. 2 and Table 5, the weights of WAT (abdominal, epididymal and inguinal adipose tissues) were markedly reduced in the experimental groups treated with extracts or fractions from G. max leaves in comparison with the control (HFHC) group, and the calculated total WAT weights also markedly reduced in those groups. The total WAT weights of ND group fed with a normal diet for 12 weeks were 168.2±0.4 g/kg body weight. The total WAT weights of control group were increased significantly to 206.7±6.0 g/kg body weight. In the meantime, the total WAT weights of experimental group 1 fed with the ethanol extract of G. max leaves was 137.0±25.6 g/kg body weight, indicating significant inhibition of body fat gaining. Such the inhibitory effects of body fat gaining were similarly observed in experimental groups 2~4 treated with the extracts of G. max leaves or fractions isolated from the same.

<4-3> Measurement of Total Hepatic Lipid Contents

The total hepatic lipid in liver taken from mice of Experimental Example <4-1> was extracted using organic solvents according to the method of Folch et al. (J. Biol. Chem. 226: 497-509, 1957). The extracted total hepatic lipid was concentrated and dried down under a reduced pressure, and measured the weights. The results are shown in Table 6.

TABLE 6

| Experimental groups | Total hepatic lipid contents (mg/g liver) |
|---|---|
| Normal diet group (ND) | 109 ± 5 |
| Control group (HFHC) | 145 ± 11 |
| Experimental group 1 (HFHC + ethanol extracts of G. max leaves, EGML) | 117 ± 11 |
| Experimental group 2 (HFHC + water extracts of G. max leaves) | 125 ± 9 |
| Experimental group 3 (HFHC + hexane fractions of G. max leaves) | 120 ± 12 |
| Experimental group 4 (HFHC + ethyl acetate fractions of G. max leaves) | 112 ± 10 |

As shown in Table 5, the content of total hepatic lipid of ND group was 109±5 mg/g liver, while that of control group was 145±11 mg/g liver. In the meantime, that of experimental group 1 (EGML) treated with the ethanol extracts of G. max leaves was significantly decreased (117±11 mg/g liver). Similar decrease of total hepatic lipid contents (14-23%) were observed in experimental groups 2~4 treated with the extracts of G. max leaves or fractions isolated from the same.

The extracts and fractions of G. max leaves of the present invention inhibit the increase of body fat and reduce the accumulation of total hepatic lipid, suggesting that they can be effectively used for the prevention and treatment of obesity and fatty liver.

Experimental Example 5

Plasma Biomarker Analysis

The levels of plasma biomarkers, total cholesterol, high-density lipoprotein (HDL)-cholesterol, triglyceride, glucose, GOT, and GPT were measured using an automatic blood biochemical analyzer (Hitachi-720, Hitachi Medical, Japan) with blood collected from each mouse of Experimental Example <4-1>. The levels of plasma insulin were determined using a radioimmunoassay kit.

<5-1> Measurements of Plasma Lipids

After 12-week experiment, the plasma concentrations of total cholesterol (TC), HDL-cholesterol (HDL-C), triglyceride (TG) and phospholipid (PL) were measured and the results are shown in Table 7.

TABLE 7

| Experimental groups | TC (mg/dl) | HDL-C/TC (%) | TG (mg/dl) | PL (mg/dl) |
|---|---|---|---|---|
| ND | 477 ± 35 | 29.5 ± 1.8 | 225 ± 46 | 482 ± 23 |
| Control (HFHC) | 1143 ± 93 | 12.3 ± 0.6 | 385 ± 37 | 741 ± 50 |
| Experimental group 1 | 900 ± 63 | 16.5 ± 1.2 | 303 ± 81 | 664 ± 54 |
| Experimental group 2 | 972 ± 66 | 16.0 ± 1.1 | 323 ± 39 | 682 ± 56 |
| Experimental group 3 | 915 ± 60 | 16.4 ± 1.0 | 311 ± 55 | 662 ± 50 |
| Experimental group 4 | 800 ± 58 | 17.1 ± 1.2 | 295 ± 40 | 630 ± 34 |

As shown in Table 7, total cholesterol (TC) of ND group was 477±35 mg/dl, and that of control group was 1143±93 mg/dl. In the meantime, TC of experimental group 1 fed with the diet supplemented with the ethanol extract of G. max leaves was reduced to 900±63 mg/dl (P<0.05). The ratio of HDL-C to TC was 29.5±1.8% in ND group and 12.3±0.6% in control group, while the ratio was increased in experimental group 1 (EGML) to 16.5±1.2% (P<0.01). This result means that the atherosclerotic index of experimental group 1 (EGML) was decreased in comparison with that of the control (HFHC) group. Triglyceride (TG) of ND group was 225±46 mg/dl, and TG of control group was 385±37 mg/dl. A 12-week administration of the ethanol extracts of G. max leaves decreased markedly the level of TG to 303±81 mg/dl (P<0.05) in experimental group 1. Phospholipid (PL) of ND group was 482±23 mg/dl, and that of control group was 741±50 mg/dl. On the other hand, the PL level of experimental group 1 (EGML) was reduced to 664±54 mg/dl (P<0.05). Similarly to experimental group 1 (EGML), the TC levels were reduced (15~30%) in experimental groups 2~4 treated with the extracts and fractions of G. max leaves, and the ratio of HDL-C to TC was increased (30~39%). The TG and PL levels were reduced 16~23% and 8~15%, respectively, in those groups.

<5-2> Measurements of Plasma Glucose and Insulin

After 12-week experiment, the plasma levels of glucose and insulin were measured and the results are shown in Table 8.

TABLE 8

| Experimental groups | Glucose (mg/dl) | Insulin (ng/ml) |
|---|---|---|
| ND | 125 ± 34 | 0.584 ± 0.059 |
| Control (HFHC) | 173 ± 25 | 0.773 ± 0.158 |
| Experimental group 1 | 154 ± 33 | 0.640 ± 0.102 |
| Experimental group 2 | 157 ± 31 | 0.657 ± 0.112 |
| Experimental group 3 | 155 ± 28 | 0.643 ± 0.095 |
| Experimental group 4 | 145 ± 30 | 0.611 ± 0.088 |

As shown in Table 8, the levels of plasma glucose were 125±34 mg/dl in ND group and 173±25 mg/dl in control group, respectively. On the other hand, the plasma glucose level of experimental group 1 (EGML) treated with the ethanol extracts of *G. max* leaves was reduced to 154±33 mg/dl. The levels of plasma insulin were 0.584±0.059 ng/ml in ND group and 0.773±0.158 ng/ml in control group, respectively, while the plasma glucose level of experimental group 1 reduced to 0.640±0.102 ng/ml. Similarly to the experimental group 1, the levels of plasma glucose and insulin were reduced 9~16% and 15~21%, respectively, in experimental groups 2~4 treated with the extracts and fractions of *G. max* leaves.

<5-3> Measurements of Hepatotoxic Indexes in Plasma

After 12-week experiment, the plasma levels of hepatotoxic indexes, GOP (aspartate transaminase, AST) and GPT (alanine transaminase, ALT) were measured and the results are shown in Table 9.

TABLE 9

| Experimental groups | GOT (IU/L) | GPT (IU/L) |
|---|---|---|
| ND | 90 ± 9 | 32 ± 12 |
| Control (HFHC) | 150 ± 35 | 74 ± 32 |
| Experimental group 1 | 128 ± 27 | 54 ± 21 |
| Experimental group 2 | 131 ± 30 | 58 ± 21 |
| Experimental group 3 | 127 ± 28 | 55 ± 18 |
| Experimental group 4 | 122 ± 25 | 47 ± 15 |

As shown in Table 9, the levels of plasma GOT were 90±9 IU/L in ND group and 150±35 IU/L in Control group, respectively. On the other hand, the plasma GOT level of experimental group 1 treated with the ethanol extracts of *G. max* leaves (EGML) was reduced to 128±27 IU/L. the levels of plasma GPT were 32±12 IU/L in ND group and 74±32 IU/L in control group, respectively, while the plasma GPT level of experimental group 1 reduced to 54±21 IU/L. Similarly to the experimental group 1, the levels of plasma GOT and GPT were reduced 13~19% and 22~36%, respectively, in experimental groups 2~4 treated with the extracts and fractions of *G. max* leaves.

Therefore, the extracts and fractions of *G. max* leaves of the present invention reduce the GOT and GPT levels, hepatic total lipid, plasma levels of total cholesterol, HDL-cholesterol, and triglyceride as well, so that they can be effectively used for the prevention or treatment of fatty liver and obesity. In addition, the extracts and fractions of *G. max* leaves of the present invention reduce the levels of plasma glucose and insulin, so that they can be effectively used for the prevention or treatment of diabetes and metabolic syndrome.

Experimental Example 6

Anti-Atherosclerotic Effects

Following experiment was performed to investigate the effect of the extracts of *G. max* leaves or fractions isolated from the same of the present invention on atherosclerosis.

Hearts from the mice were processed by the method described by Paigen et al. (Atherosclerosis, 68:231, 1987) with a slight modification. Immediately after opening the thoracic cavity, the aorta of mice of control group and experimental group 1 were excised. All samples were embedded in a Tissue-Tek OCT compound (Sakura Finetek, Inc., Torrance, Calif.) and were placed on a cryotome model AS620 (Shandon, Pittsburgh, Pa.). Cryostat sections of aortic roots (10 μm) were collected and stained with oil red 0 (Gulledgr, A A, et al., Arteioscler. Thromb. Vasc, Biol. 23:130-135, 2003). For accurate lesion analysis, aortic sinus region was divided into a distal portion which was close to the heart and a proximal portion which was far from the heart. Aortic images were captured with a BX61 microscope (Olympus, JAPAN), and atherosclerotic lesions were quantified by computer image analysis using Metamorph imaging software (Molecular devices, Japan). The results are shown in Table 10.

TABLE 10

| | | Control (n = 10) | Experimental group 1 (n = 10) | *P |
|---|---|---|---|---|
| aortic sinus lesions (distal portion) | Lesion size ($\mu m^2 \times 10^3$) | 129.6 ± 45.7 | 70.3 ± 53.9 | 0.01243 |
| | Lesion/whole aortic sinus | 39.0 ± 13.4 | 16.0 ± 10.1 | 0.00062 |
| aortic sinus lesions (proximal portion) | Lesion size ($\mu m^2 \times 10^3$) | 141.4 ± 56.3 | 58.2 ± 32.9 | 0.00060 |
| | Lesion/whole aortic sinus | 37.7 ± 8.9 | 14.3 ± 9.3 | 0.00003 |

*P < 0.05: statically significant

As shown in Table 10, the mean oil red O-stained lesional areas in distal portion were (129.6±45.7) $\mu m^2 \times 10^3$ in control group and (70.3±53.9) $\mu m^2 \times 10^3$ in experimental group 1 treated with the extracts of *G. max* leaves (EGML) of the present invention. The ratios of these stained areas to those of the lesion size for the entire aortic sinus were calculated. As a result, the lesion/whole aortic sinus ratios in distal portion were 39.0±13.4 in control group and 16.0±10.1 in experimental group, indicating that the administration of the EGML reduced the lesion formation to 46%.

In proximal portion, the mean oil red O-stained lesional areas in distal portion were (141.4±56.3) $\mu m^2 \times 10^3$ in control group and (58.2±32.9) $\mu m^2 \times 10^3$ in experimental group 1. The lesion/whole aortic sinus ratios in proximal portion were 37.7±8.9 in control group and 14.3±9.3 in experimental group, indicating that the administration of the EGML reduced effectively the lesion formation to 62%.

Therefore, the extracts of *G. max* leaves or fractions isolated from the same of the present invention reduce the aortic lesion formation, so that they can be effectively used for the prevention or treatment of atherosclerosis.

The Manufacturing Examples of the composition for the present invention are described hereinafter.

Manufacturing Example 1

Preparation of Pharmaceutical Formulations

<1-1> Preparation of Powders

| | |
|---|---|
| Extracts of *G. max* leaves or fractions isolated from the same | 2 g |
| Lactose | 1 g |

Powders were prepared by mixing all the above components, which were filled in airtight packs according to the conventional method for preparing powders.

<1-2> Preparation of Tablets

| | |
|---|---|
| Extracts of *G. max* leaves or fractions isolated from the same | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Extracts of *G. max* leaves or fractions isolated from the same | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Extracts of *G. max* leaves or fractions isolated from the same | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Extracts of *G. max* leaves or fractions isolated from the same | 150 mg |
| Soybean extracts | 50 mg |
| Glucose | 200 mg |
| Starch | 600 mg |

All the above components were mixed, to which 100 mL of 30% ethanol was added. The mixture was dried at 60° C. and the prepared granules were filled in packs.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating obesity or diabetes comprising the step of administering a therapeutically effective dose of an extract of *Glycine max* leaves to a subject in need of said treatment, wherein the extract is prepared by a process consisting essentially of:
an extraction step performed on *Glycine max* leaves using water, organic solvent or a mixed solvent thereof.

2. The method for treating obesity or diabetes according to claim 1, wherein the organic solvent is alcohol, ethyl acetate or acetonitrile.

3. The method for treating obesity or diabetes according to claim 2, wherein the alcohol is methanol, ethanol, propanol or isopropanol.

4. A method for treating obesity or diabetes comprising the step of administering a therapeutically effective dose of an organic solvent fraction to a subject, wherein the organic solvent fraction is prepared by a process consisting essentially of:
an extraction step performed on *Glycine max* leaves using water, organic solvent or a mixed solvent thereof to produce an extract of *Glycine max* leaves, and, a step of fractioning the extract using an organic solvent.

5. The method for treating obesity or diabetes according to claim 4, wherein the organic solvent is hexane or ethyl acetate.

6. The method according to claim 1, wherein the method consists essentially of a step of administering a therapeutically effective dose of said extract.

7. The method according to claim 4, wherein the method consists essentially of a step of administering a therapeutically effective dose of said extract.

8. The method according to claim 1, wherein the *Glycine max* leaves are obtained after 90 days after growing.

9. The method according to claim 4, wherein the *Glycine max* leaves are obtained after 90 days after growing.

10. A method for treating obesity or diabetes comprising the step of administering a therapeutically effective dose of an extract of *Glycine max* leaves to a subject in need of said treatment, wherein the extract is prepared by a process comprising:
an extraction step performed on *Glycine max* leaves using water, organic solvent or a mixed solvent thereof, and the extract comprises: kaempferol-3-O-α-L-rhamnopyranosyl(1→2)-β-D-glucopyranosyl(1→6)-β-D-galactopyranoside; kaempferol-3-O-(2,6-di-O-α-rhamnopyranosyl)-β-galactopyranoside; kaempferol-3-O-digalactopyranoside; kaempferol-3-O-α-L-rhamnopyranosyl(1→6)-β-D-galactopyranoside; kaempferol-3-O-rutinoside; and genistin.

11. A method for treating obesity or diabetes comprising the step of administering a therapeutically effective dose of the organic solvent fraction to a subject, wherein the organic solvent fraction is prepared by a process comprising:
an extraction step performed on *Glycine max* leaves using water, organic solvent or a mixed solvent thereof to produce an extract of *Glycine max* leaves, and, a step of fractioning the extract using an organic solvent, and the fraction comprises: kaempferol-3-O-α-L-rhamnopyranosyl(1→2)-β-D-glucopyranosyl(1→6)-β-D-galactopyranoside; kaempferol-3-O-(2,6-di-O-α-rhamnopyranosyl)-β-galactopyranoside; kaempferol-3-O-digalactopyranoside; kaempferol-3-O-α-L-rhamnopyranosyl(1→6)-β-D-galactopyranoside; kaempferol-3-O-rutinoside; and genistin.

* * * * *